United States Patent [19]

Eiserman et al.

[11] Patent Number: 4,558,696
[45] Date of Patent: Dec. 17, 1985

[54] WATER TRAP

[76] Inventors: Gary K. Eiserman, Physics Bldg., University of Virginia, McCormick Rd., Charlottesville, Va. 22901; Robert W. Hagar, 1503 Fulton Ave. #79, Sacramento, Calif. 95825

[21] Appl. No.: 600,242

[22] Filed: Apr. 16, 1984

[51] Int. Cl.$^4$ .............................. A61M 16/00
[52] U.S. Cl. .................. 128/205.12; 55/466; 55/452
[58] Field of Search .......... 128/205.12, 205.27; 55/461, 466, 319, 458, 452

[56] References Cited

U.S. PATENT DOCUMENTS

| | | | |
|---|---|---|---|
| 2,458,909 | 1/1949 | John | 55/319 |
| 3,968,812 | 7/1976 | Eross | 137/188 |
| 4,020,834 | 5/1977 | Bird | 128/205.12 |
| 4,327,718 | 5/1982 | Cronenberg | 128/205.12 |
| 4,391,271 | 7/1983 | Blanco | 128/205.12 |

*Primary Examiner*—Henry J. Recla
*Attorney, Agent, or Firm*—Beveridge, DeGrandi & Weilacher

[57] ABSTRACT

The present invention is a liquid water trap for continuous trapping of liquid from the gas passed by a pressurized breathing circuit of a ventilator, respirator, anaesthesia unit or the like. A hollow, spherically shaped member has a plurality of holes through its surface. A pair of tubular members extend from within the spherically shaped member, through the surface thereof, and radially outward therefrom, with the first end of each tubular member positioned within the spherically shaped member such that the first ends are separated and overlap in the central region of the spherically shaped member. The second ends of the pair of tubular members are adapted for connection in a pressurized breathing circuit for passage of the breathing circuit gas therethrough. A drain tube member is wrapped about the exterior of the spherically shaped member and has a smaller diameter than the pair of tubular members, with a plurality of holes on one side only of the drain tube member, the drain tube holes being substantially the same size as and overlying the spherically shaped member holes, so that liquid water lying in the lowest lying region within the spherically shaped member flows through the spherically shaped member holes and the drain tube holes and drains out the drain tube.

5 Claims, 1 Drawing Figure

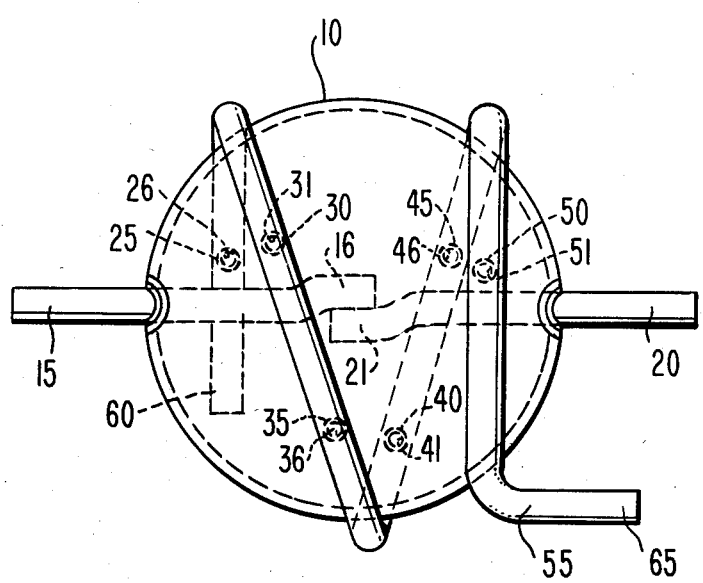

WATER TRAP

BACKGROUND OF THE INVENTION

The present invention pertains to a water trap for removing liquid water from the pressurized breathing circuit of a ventilator, respirator, anaesthesia unit, or similar device. In such devices, gas mixtures containing water vapor are delivered under pressure to a patient. Water vapor is added so that the inspired gases do not dry out the patient's lungs. Since the temperature of the air outside the gas line is lower than the temperature of the gas mixture inside, water vapor in the gas line partially condenses to form liquid water. Therefore, to prevent liquid water from entering the patient's lungs it is necessary to have some means for trapping, and permanently removing, the liquid water from the gas line.

Previous water traps, though useful, have been deficient in several important respects. Many water traps quickly fill up with water and then must be drained. Often the breathing circuit is interrupted while the trap is being emptied. Another problem with these prior traps is that valuable hospital staff time must be spent on monitoring and emptying the traps. Many small water traps require draining every hour, and clearly, the smaller the trap, the more frequently the trap must be drained. Small traps also pose the hazard that if the trap is disturbed, by patient movement or some other source, then water may be projected into the gas line and into the patient's lungs. Thus, with such prior art water traps it is advantageous to have the liquid water quickly and permanently removed from the trap so as to reduce the possibility of this occurrence.

If the trap is large, so as to reduce the frequency of monitoring and draining, then a substantial strain on the gas line results from the accumulated weight of the water. This weight restricts patient movement and may actually deform the gas line. Additionally, use of a large trap makes it necessary for the ventilator or other device to work harder, since a larger volume must be pressurized.

A further problem with previous traps relates to their configuration. The typical trap consists of a "T" in the gas line, with the water storage receptacle connected to the bottom portion. Such a configuration requires that the trap be oriented in a vertical or close to vertical position for proper functioning. If the trap is not so oriented, draining will be substantially impaired, and perhaps cease. This creates the hazard that upon any minor disturbance of the trap, from patient movement or any other source, water may be projected into the gas line and into the patient's lungs. Certainly, it would be a substantial contribution to have a trap which can continuously trap and drain liquid water, thereby permitting uninterrupted operation of the breathing circuit, and which can function in any orientation. As described below, the present invention possesses all of these advantages.

Those few water traps which do allow for continuous operation of the breathing circuit require a specific orientation for proper functioning. One such trap, as disclosed in U.S. Pat. No. 4,327,718, utilizes a membrane which is gas impervious and liquid pervious, with a receptacle for receiving the liquid water lying under the membrane. Such a configuration, though allowing for continuous draining and operation of the breathing circuit, necessitates that the trap be oriented in a vertical or close to vertical position for proper functioning.

Another trap, disclosed in U.S. Pat. No. 3,968,812, relies on a highly sensitive diaphragm Water accumulates on the diaphragm until the weight of the water causes the diaphragm to unseat, and the water then passes to a collecting bag. Clearly, in a crowded hospital room setting, where many large and cumbersome pieces of equipment may be present, the patient's safety is threatened if the water trap is not oriented properly by a hospital staff member, or, if once oriented properly, it then moves from its vertical orientation because of patient movement or some other disturbance. Additionally, hospital staff time is wasted rearranging equipment to provide for the necessary vertical orientation of the trap. Additionally, the diaphragm's proper functioning requires frequent checking and maintenance.

SUMMARY OF THE INVENTION

The present invention is a liquid water trap for continuous trapping of liquid from the gas passed by a pressurized breathing circuit of a ventilator, respirator, anaesthesia unit or the like. A hollow, spherically shaped member has a plurality of holes through its surface. A pair of tubular members extend from within the spherically shaped member, through the surface thereof, and radially outward therefrom, with the first end of each tubular member positioned within the spherically shaped member such that the first ends are separated and overlap in the central region of the spherically shaped member. The second ends of the pair of tubular members are adapted for connection in a pressurized breathing circuit for passage of the breathing circuit gas therethrough. A drain tube member is wrapped about the exterior of the spherically shaped member and has a smaller diameter than the pair of tubular members, with a plurality of holes on one side only of the drain tube member, the drain tube holes being substantially the same size as and overlying the spherically shaped member holes, so that liquid water lying in the lowest lying region within the spherically shaped member flows through the spherically shaped member holes and the drain tube holes and drains out the drain tube. Since the trap has a spherical shape, it can be oriented in any manner and still function properly. An additional feature of the trap is the provision for continuous draining and uninterrupted operation of the breathing circuit. A further advantage of the trap is that it is adaptable to a suction device which quickly and permanently removes the liquid water from the trap. These features allow for substantial savings in hospital staff time and effort, as well as improved patient safety.

BRIEF DESCRIPTION OF THE DRAWING

These and other aspects and advantages of the present invention are more apparent from the following detailed description and claims, particularly when considered in conjunction with the accompanying drawing which is a plan view of one preferred embodiment of a water trap in accordance with the present invention.

DETAILED DESCRIPTION OF THE PREFERRED EMBODIMENT

As seen in the drawing, the water trap of the present invention includes a hollow, light-weight, plastic sphere 10 with tubes 15 and 20 passing from the sphere interior, through the sphere wall to extend radially from the sphere. Tubes 15 and 20 are positioned within sphere 10 so that the tube ends 16 and 21 are separated and short sections of the tubes overlap in the central region of sphere 10. The diameter of tubes 15 and 20 is approximately the same as the diameter of the gas lines from the ventilator, respirator, anaesthesia unit or other device and to the patient, permitting connection of the water trap to those gas lines. Tube 15 is attached by suitable connectors, known to the art, to that part of the gas line which leads from the ventilator, respirator, anaesthesia unit or other device, while tube 20 is attached, by suitable connectors known to the art, to that part of the gas line which leads to the patient. The trap's symmetry, of course, allows the tubes to be reversed without any impairment in function.

A number of holes, depicted in the drawing as six holes 25, 30, 35, 40, 45, and 50, pass through the surface of sphere 10. A drain tube 55, of a smaller diameter than tubes 15 and 20, is wound around sphere 10. Tube 55 has holes 26, 31, 36, 41, 46, and 51 through one side of it, of a number equal to the number of holes 25-50 through the surface of sphere 10. Tube 55 is wound around, and attached to, sphere 10 in such a manner that the holes 26-51 in tube 55 overlie the holes 25-50 of sphere 10. End 60 of tube 55 is open, and end 65 is attached by suitable connectors to a suction line, commonly found in hospital rooms, which draws the contents of tube 55 into a drain. In the preferred embodiment the diameter of the holes 25-51 is approximately the size of a single water drop. This diameter makes it impossible for air to move through narrow tube 55 without carrying water along with it. Holes 25-51 are positioned around the surface of sphere 10 in such a manner that, no matter the orientation of the water trap, the level of water within the trap reaches one or more of the sets of holes 25-51 before it reaches the tube ends 16 and 21. This arrangement of the holes results in draining of liquid from sphere 10 no matter what the orientation of the water trap happens to be. Though there will be a small air loss through holes 25-51, that loss can easily be compensated for by increasing the volume of air delivered by the ventilator or other such device.

With reference to the drawing, in operation of the water trap, liquid water which has condensed in tube 15 drips out of tube end 16 into the lowest lying region of sphere 10 where the water then collects. The overlap of tubes 15 and 20 is such that liquid water cannot drip from one tube into the other. The water continues to collect until it reaches the level of the lowest lying one of the holes 25, 30, 35, 40, 45 or 50. The water then flows, aided by suction, through that hole and the corresponding hole 26, 31, 36, 41, 46, or 51 of drain tube 55 into the interior of tube 55. The suction in tube 55 causes the water to flow through tube 55, out its end 65, and to a drain.

In this embodiment of the water trap end 60 of tube 55 remains open to provide air for the suction device. Since the air pressure in the trap never falls below atmospheric pressure, liquid water never backs up into the trap from the drain line. The liquid water never collects above the level of the lowest lying hole 25-51, and the water is permanently removed from the trap by means of drain tube 55. Thus, the possibility of projecting water, because of patient movement or other disturbance, into tubes 15 and 20 is eliminated. Moreover, since water is quickly and permanently removed, only a minimal strain exists on the gas line because of the weight of the accumulated water. Additionally, because the trap does not have to be shut down and removed for emptying of water therefrom, uninterrupted operation of the breathing circuit is possible.

Holes 25-51 are positioned so that regardless of the orientation of sphere 10, the liquid water level reaches one or more sets of the holes 25-51 before the water level reaches the ends 16 and 21 of tubes 15 and 20. Consequently, even if sphere 10 is caused to rotate, because of patient movement or for other reasons, water collects in sphere 10 only until it reaches such lowest lying holes from which it passes into drain tube 55. Consequently, all liquid water which flows into the trap will be caught by the trap and permanently removed therefrom. The number of holes 25-51 in sphere 10 and drain tube 55 can be increased or decreased as desired so as to control the level to which water can accumulate within sphere 10. Water trap 10 can also be operated with end 65 of drain tube 55 connected directly to a drain, without using a suction device. In such an embodiment, end 60 of drain tube 55 should be closed to prevent water from draining therefrom. End 60 of drain 55 might likewise be closed even with a suction device attached to end 65 of the tube, although it is presently preferred to have end 60 open during such operation.

Although the present invention has been described with reference to preferred embodiments, rearrangements and alterations could be made, and still the result would be within the scope of the invention.

What is claimed is:

1. A liquid water trap for continuous trapping of liquid from the gas passed by a pressurized breathing circuit of a ventilator, respirator, anaesthesia unit or the like, comprising:
   a hollow, spherically shaped member having a plurality of holes through the surface thereof;
   a pair of tubular members extending from within said spherically shaped member, through the surface thereof, and radially outward therefrom with the first end of each tubular member positioned within said spherically shaped member such that said first ends are separated and overlap in the central region of said spherically shaped member, the second ends of said pair of tubular members being adapted for connection in a pressurized breathing circuit for passage of the breathing circuit gas therethrough;
   a drain tube member wrapped about the exterior of said spherically shaped member and having a smaller diameter than said pair of tubular members, with a plurality of holes on one side only of said drain tube member, the drain tube holes being substantially the same size as and overlying the spherically shaped member holes, so that liquid water lying in the lowest lying region within the spherically shaped member flows through the spherically shaped member holes and the drain tube holes and drains out said drain tube.

2. The device of claim 1 wherein said drain tube has a first open end and a second end adapted for attachment to a suction device or a drain.

3. The device of claim 2 wherein the size of the spherically shaped member holes and the drain tube holes is approximately the size of a single water drop.

4. The device of claim 1 wherein said drain tube has a first closed end and a second end adapted for attachment to a suction device or a drain.

5. The device of claim 4 wherein the size of the spherical member holes and the drain tube holes is approximately the size of a single water drop.

* * * * *